United States Patent
Sinha

[11] Patent Number: 5,886,262
[45] Date of Patent: Mar. 23, 1999

[54] APPARATUS AND METHOD FOR COMPARING CORRESPONDING ACOUSTIC RESONANCES IN LIQUIDS

[75] Inventor: Dipen N. Sinha, Los Almos, N. Mex.

[73] Assignee: The Regents of The University of California, Los Alamos, N. Mex.

[21] Appl. No.: 218,102

[22] Filed: Mar. 25, 1994

[51] Int. Cl.[6] ................................................. G01N 29/12
[52] U.S. Cl. ............................................... 73/579; 73/592
[58] Field of Search ............................ 73/579, 592, 620, 73/627, 632, 645, 646, 648, 659

[56] References Cited

U.S. PATENT DOCUMENTS

| | | | |
|---|---|---|---|
| 4,391,129 | 7/1983 | Trinh et al. | 73/579 |
| 4,771,792 | 9/1988 | Seale | 73/575 |
| 4,991,124 | 2/1991 | Kline | 73/579 |
| 5,062,296 | 11/1991 | Migliori | 73/579 |
| 5,259,250 | 11/1993 | Kolpak | 73/861.38 |
| 5,359,541 | 10/1994 | Pope et al. | 73/32 A |
| 5,426,977 | 6/1995 | Johnston et al. | 73/579 |

*Primary Examiner*—Max H. Noori
*Attorney, Agent, or Firm*—Samuel M. Freund

[57] ABSTRACT

Apparatus and method for comparing corresponding acoustic resonances in liquids. The present invention permits the measurement of certain characteristics of liquids which affect the speed of sound therein. For example, a direct correlation between the octane rating of gasoline and the speed of sound in a gasoline sample has been experimentally observed. Therefore, changes in the speed of sound therein can be utilized as a sensitive parameter for determining changes in composition of a liquid sample. The present apparatus establishes interference patterns inside of a liquid without requiring the use of very thin, rigorously parallel ceramic discs, but rather uses readily available piezoelectric transducers attached to the outside surface of the usual container for the liquid and located on the same side thereof in the vicinity of one another. That is, various receptacle geometries may be employed, and the driving and receiving transducers may be located on the same side of the receptacle. The cell may also be constructed of any material that is inert to the liquid under investigation. A single-transducer embodiment, where the same transducer provides the excitation to the sample container and receives signals impressed therein, is also described.

5 Claims, 5 Drawing Sheets

APPARATUS AND METHOD FOR COMPARING CORRESPONDING ACOUSTIC RESONANCES IN LIQUIDS

This invention was made with Government support under Contract No. W-7405-ENG-36 awarded by the U.S. Department of Energy. The Government has certain rights in the invention.

BACKGROUND OF THE INVENTION

The present invention relates generally to measurement of acoustic resonances in liquids and, more particularly, to the identification of certain properties of liquids through the comparison of their corresponding acoustic resonant frequencies.

Various state and federal laws require that the octane ratings posted on gasoline pumps at gas stations are within certain limits of accuracy. Octane rating is a number indicating the degree of knocking of a fuel mixture under standard test conditions. To prevent the fuel-wasting, potentially damaging engine knock at all engine speeds and loads, gasoline must have high antiknock quality (octane number) throughout its entire distillation range.

Early in the study of engine knocking, it was recognized that the chemical structure of fuel hydrocarbons largely determines their tendency to cause knock, and that straight-chain paraffins are more prone to knocking than branched-chain paraffins, olefins, or cyclic hydrocarbons. Soon after the discovery of antiknock additive agents, it became evident that a yardstick was needed for measuring the antiknock quality of motor fuels. In 1926, Ethyl Corporation developed the octane scale, which has become the worldwide standard for that purpose. For the zero of the scale, a straight-chain hydrocarbon, n-heptane, is selected since it burns with considerable knock. For 100, a non-knocking branched-chain hydrocarbon 2,2,4-trimethylpentane (often incorrectly referred to as isooctane) is chosen. By blending these two hydrocarbons in varying percentages, a primary reference fuel can be produced to match the knock resistance of any gasoline sample. Octane number is defined as the percentage of isooclane required in a blend with n-heptane to match the knocking behavior of the gasoline being tested. Thus, if a blend of 87% 2,2,4-trimethylpentane and 13% n-heptane is required to match the knock resistance of a particular gasoline sample when both are run in a test engine under specified conditions, the sample is said to have an octane number of 87.

The CFR (Cooperative Fuel Research) knock-test engine has been adopted as the standard for determining octane number. Basically, it is a single-cylinder, four-stroke engine in which the compression ratio can be varied at will. Auxiliary equipment includes means for detecting pressure impulses from detonation, an electronic amplifier, and a meter to record knock intensity. To determine a fuel's antiknock quality, the CFR engine is operated on the fuel under a standard set of conditions, and its compression ratio is adjusted to give a standard level of knock intensity. The method is cumbersome and time-consuming, and the equipment is expensive. For frequent monitoring of gasoline octane rating at gas stations and at distillation plants, a simpler method is needed.

It has been known for several decades that it is possible to set-up acoustic interference patterns inside a liquid if the liquid is contained within two parallel-plate acoustic transducers. Generally, one uses thin quartz disks for transducers. One transducer is excited by a swept sine signal while the other transducer picks up the signal that results from interferences within the liquid at certain fixed frequencies which depend on the separation between the two transducers and the speed of sound in the liquid. The interferences are detected as resonances and can be easily observed using commercially available electronics. This conventional resonator technique as described requires very thin and fragile quartz discs which must be kept in contact with the liquid inside a chamber.

Accordingly, an object of the present invention is to provide an apparatus for comparing corresponding acoustic resonant frequencies of liquids in identical receptacles.

Another object of the invention is to provide an apparatus for determining the resonant frequencies of liquids without contacting the liquid.

Yet another object of the present invention is to determine the identity of liquids and other characteristics thereof which affect the speed of sound therein from a comparison of their corresponding acoustic resonances.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTIONS

To achieve the foregoing and other objects, and in accordance with the purposes of the present invention, as embodied and broadly described herein, the apparatus for comparing corresponding acoustic resonances in liquids may include in combination: a first transducer for applying a periodic acoustical signal to the outside of a receptacle containing the liquid; means for driving the first transducer at a chosen frequency; a second transducer located on the some side of the receptacle as the first transducer and in the vicinity thereof, for receiving the acoustical signal generated in the sample; and means for measuring the resonant frequencies received by the second transducer.

In yet another aspect of the present invention, in accordance with its objects and purposes, the method for comparing corresponding acoustic resonances in liquids includes the steps of: establishing an acoustic interference pattern in the liquid sample to be investigated by applying a periodic acoustical signal having a chosen frequency to the outside of the receptacle containing the sample; sweeping the frequency of the applied signal over a chosen frequency range; and measuring the frequency of the interference peaks in the chosen frequency range. It is preferred that the acoustical frequency range is chosen such that the difference in the interference patterns of liquid samples having different characteristics is maximized.

Benefits and advantages of the present invention include the ability to measure changes in characteristics of liquid samples related to the speed of sound therein without contacting the liquid itself. Octane rating for gasoline samples is one such example. The method is rapid, taking but a few seconds, and has excellent resolution. The apparatus is inexpensive, and can be highly portable; namely, the size of a hand-held calculator. The present apparatus is also suited for continuous monitoring of petroleum products in distillation plants and refineries. It has no moving parts, and is completely solid state.

BRIEF DESCRIPTION OF THE DRAWINGS

The accompanying drawings, which are incorporated in and form a part of the specification, illustrate two embodiments of the present invention and, together with the description, serve to explain the principles of the invention. In the drawings.

DETAILED DESCRIPTION OF THE INVENTION

Briefly, the present invention permits the measurement of certain characteristics of liquids which affect the speed of sound therein. For example, a direct correlation between the octane rating of gasoline and the speed of sound in a gasoline sample has been experimentally observed. Therefore, changes in the speed of sound can be utilized as a sensitive parameter for determining changes in composition and, in particular, the octane rating of a gasoline sample can be directly determined through speed of sound measurements instead of by the cumbersome process of quantifying the knocking quality of the gasoline. The present apparatus establishes interference patterns inside of a liquid without requiring the use of very thin, rigorously parallel ceramic discs, but rather uses readily available piezoelectric transducers attached to the outside surface of the usual container for the liquid on one side thereof. That is, various receptacle geometries may be employed, and both exciting and receiving transducers are located on the same side thereof The cell may be constructed of any material that is inert to the liquid under investigation. For example, sturdy, thin-walled materials such as metals, glass, ceramics, and plastics may be employed. A single-transducer embodiment, where the same transducer is used for applying excitation to the container and for receiving signals impressed therein, is also described.

Figure 1:
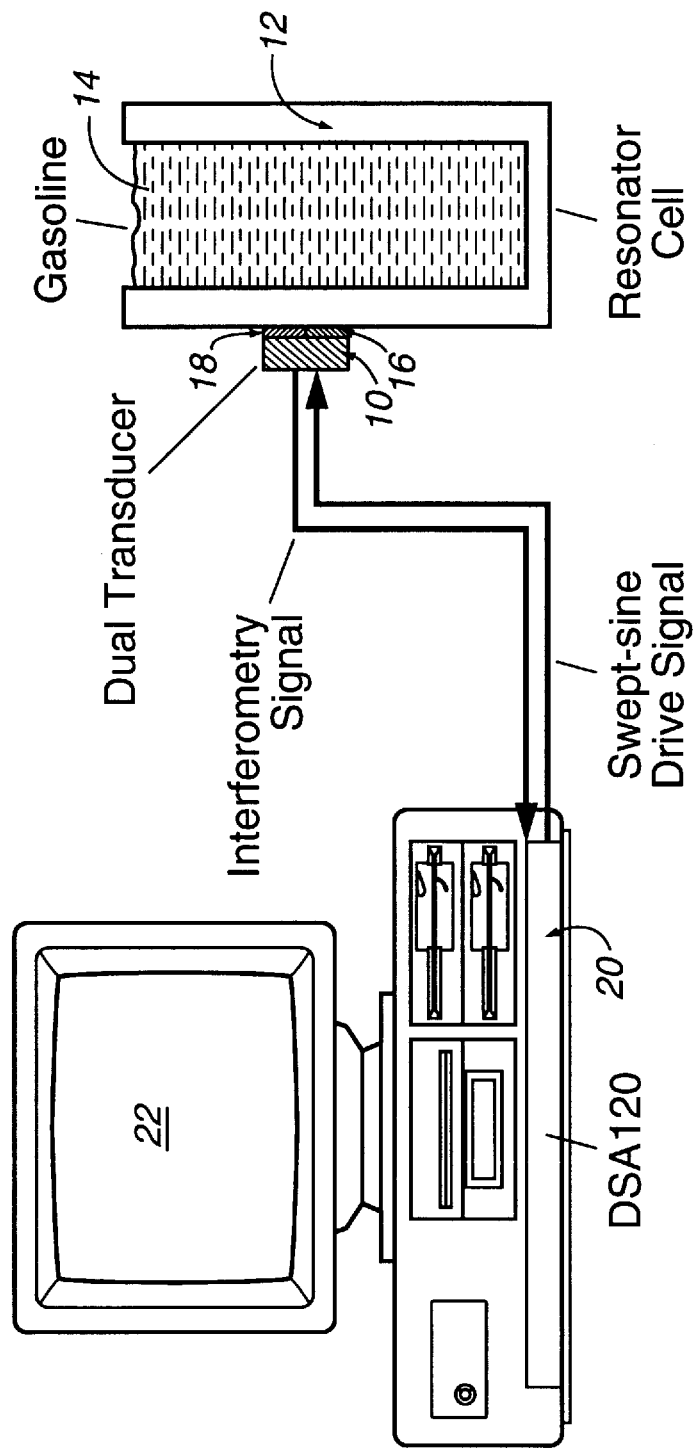
FIG. 1 is a schematic representation of one embodiment of the apparatus of the present invention, showing a dual transducer, means for periodically driving one element of the dual transducer at acoustic frequencies, means for detecting and recording the acoustic vibrations established in the liquid sample (here gasoline).

Reference will now be made in detail to the present preferred embodiments of the invention, examples of which are illustrated in the accompanying drawings. Similar or identical structure will be labeled with identical callouts. Turning now to FIG. 1, a two-transducer embodiment of the present invention is illustrated. Transducer 10, is glued in contact with the outer surface of stainless-steel receptacle 12, which contains the liquid, 14, to be analyzed. Transducer 10 may either be a dual-element transducer, where two separate transducers 16, 18 are housed in a single enclosure (as shown in the Figure), but acoustically and electrically isolated, or two completely separated transducers. The latter configuration distorts the interference peak shape, but does not affect the resonance frequencies. As stated above, both transducers are placed on the same side of the receptacle in the vicinity of one another. However, the transducers may be located on opposing walls of the receptacle as well for some applications. It is preferred that the receptacle wall thickness be small (between 1–3 mm), but larger thicknesses also may be used. One of the transducer elements serves as a transmitter of acoustical energy to the receptacle, thereby establishing vibrational motion therein while the second transducer serves as the receiver.

A Panametrics Widescan Dual Transducer Model D744 was employed for the measurements. This transducer had a 2.25 kHz center frequency, and a 0.5 in×0.5 in element size. Although the two transducers are located in the same housing, they can be used simultaneously without significant cross-talk or interference. Such transducers are generally used for high-resolution nondestructive testing of metal plates, etc. Other shapes, sizes and center-frequency transducers may also be used on the same side of the receptacle; the model identified simply provides an example. However, it is important to select a crystal having its natural resonance frequency much higher than the cavity resonance frequency to which it is attached. It should be mentioned that if two separate transducers are employed, a sharper resonance pattern is obtained if they are placed in the vicinity of one another.

Figure 2:
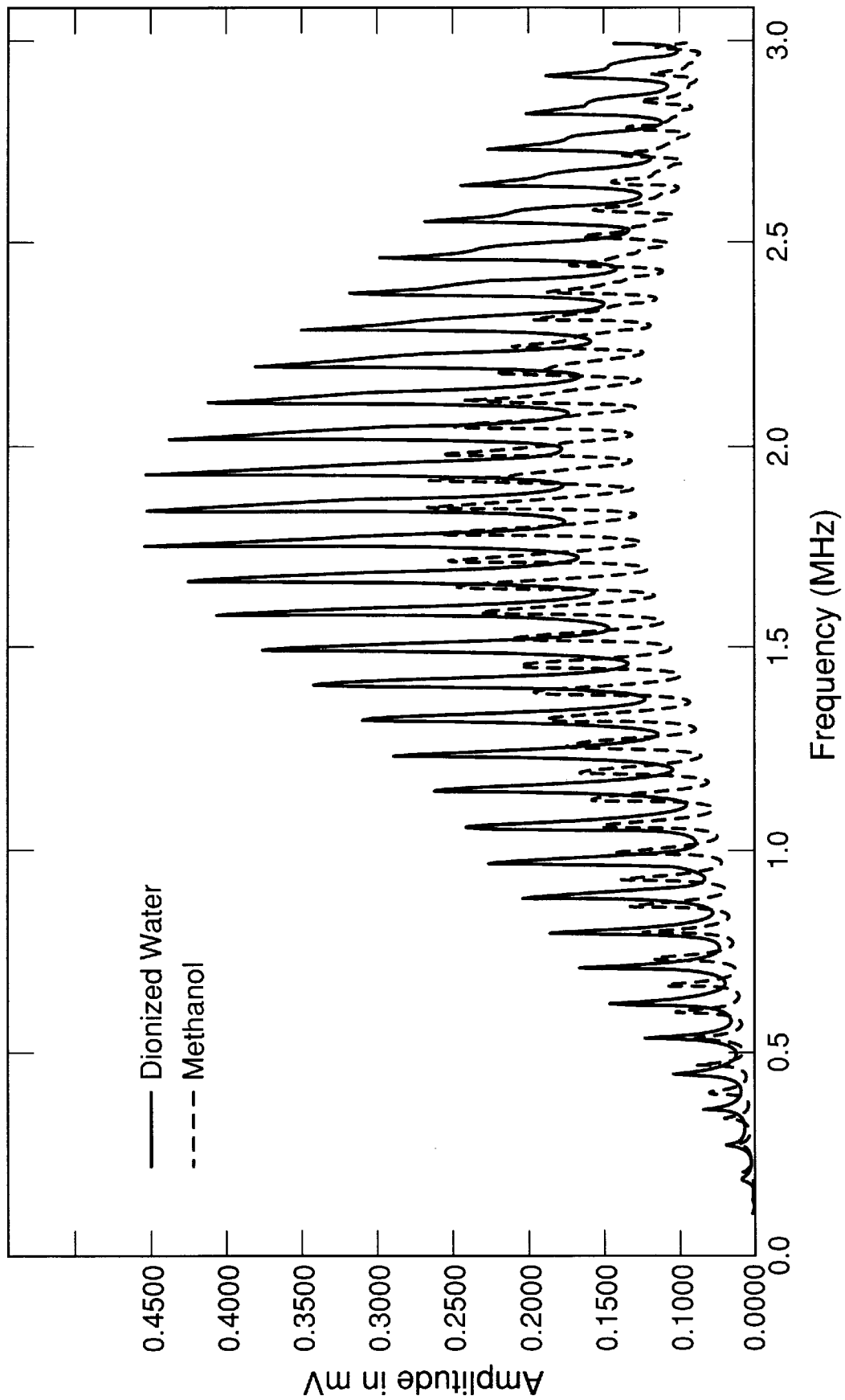
FIG. 2 shows the interference patterns generated using the apparatus described in FIG. 1 hereof, for samples of deionized water and methanol.

A Digital Synthesizer (DSA120) and Analyzer PC Plug-in board (NEEL Electronics, Laguna Niguel, Calif.), 20, was employed both to drive the transmitter and to receive the interference signal from the receiver transducer. Any electronics system capable of providing a drive signal and detecting the amplitude of the received signal may be used for these measurements. The drive signal employed is a sine wave and is swept typically from a low frequency of 200 kHz to a high frequency of 1200 kHz. A continuously applied triangle-wave or square-wave waveform would work equally well in establishing resonances in the sample. Computer 22 was used to control the synthesizer/analyzer and to receive and process the data therefrom. Interference peaks, shown in FIG. 2, represent typical data obtained from deionized water and from methanol using the apparatus described in FIG. 1 hereof. The speed of sound in a liquid is proportional to the frequency difference between any two consecutive interference peaks for that particular liquid. If corresponding data from two different liquids (i.e., two different speeds of sound) are compared, there will be a good match between the two interference patterns at certain frequencies, but they will deviate from each other at other frequencies as shown in FIG. 2. This occurs since the two patterns have different periodicity due to a difference in sound speed. Consequently, to better resolve the data between two different liquids, it is important to select a frequency range where there is a large deviation in the pattern between two liquids. For example, the measurements on gasolines were restricted to the range between 730 and 770 kHz. The optimum frequency range depends on the particular geometry (the separation between the two opposing walls) of the resonator cell. The wall separation for the cell employed in the measurements described was about 1 cm.

Figure 3:
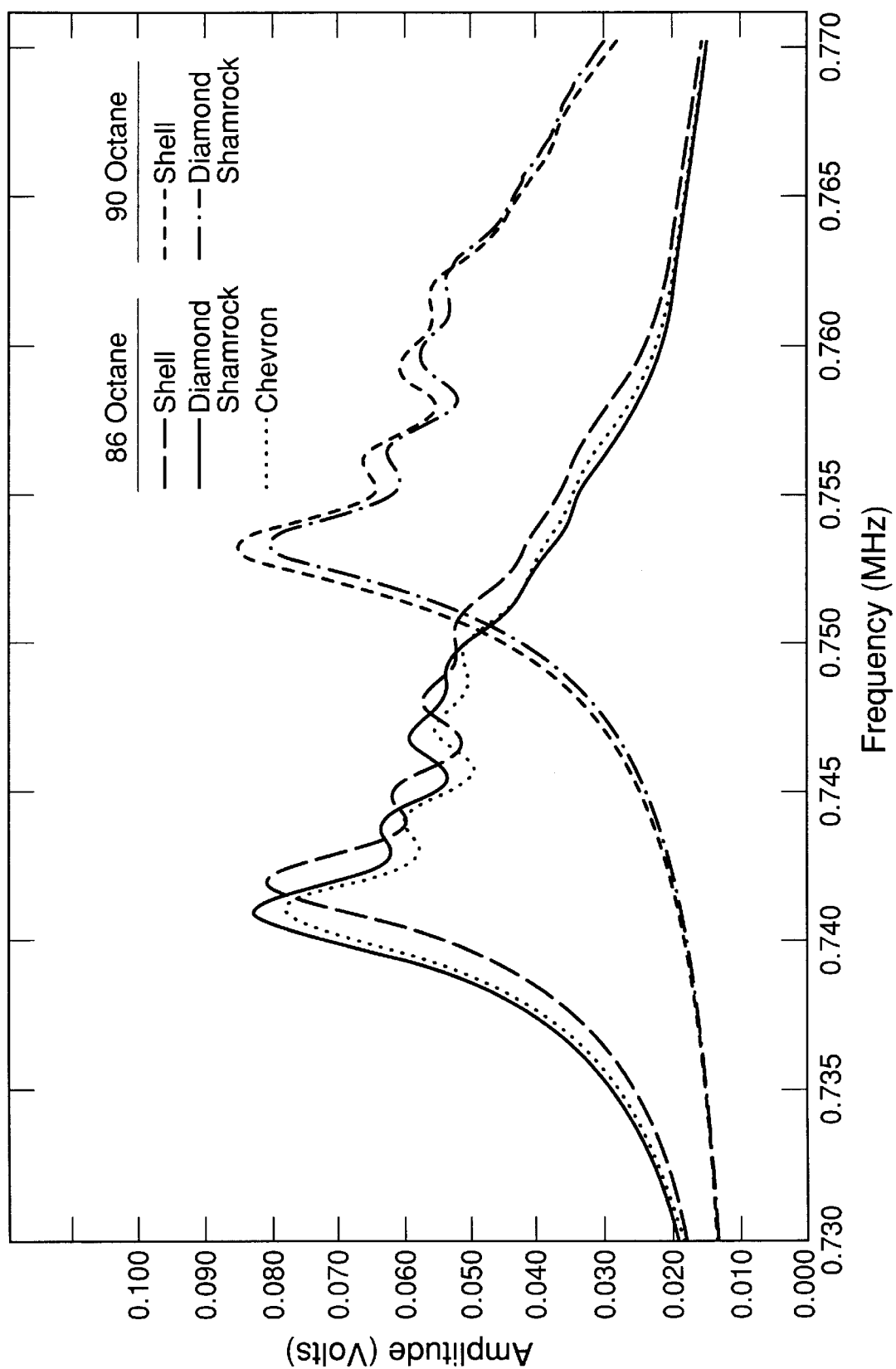
FIG. 3 shows the interference patterns generated using the apparatus described in FIG. 1 hereof, for several gasoline samples.

Gasoline having widely separated and different octane levels was introduced into receptacle 12 for the demonstration of the present invention's use in determining the octane rating of gasolines. Gasoline from three different gas companies was employed to examine the sensitivity and repeatability of the invention. FIG. 3 shows the results of the measurements. The small secondary peaks associated with each central peak are due to lack of planarity between the walls of the cell. Only a single order interference peak is shown for clarity and resolution. The 86-octane gasoline from three different manufacturers are all grouped together near 740 kHz, whereas the 90 octane ones are close 754 kHz. The difference between the two clusters of data is 14 kHz (14,000 Hz). The frequency step in the sweep frequency is 1 Hz. Thus, significant resolution in the data is possible. The shift in frequency between 86 and 90 octane gasoline is due to the change in the speed of sound. The slight variation in the 86 octane data from different manufacturers is quite understandable, since existing octane measurement techniques do not provide better than 0.5 octane resolution and the gasoline from different manufacturers can vary slightly. Additionally, different manufacturers put small amounts of additives (e.g., detergents) in their gasoline, which will slightly affect the measurements.

Figure 4:
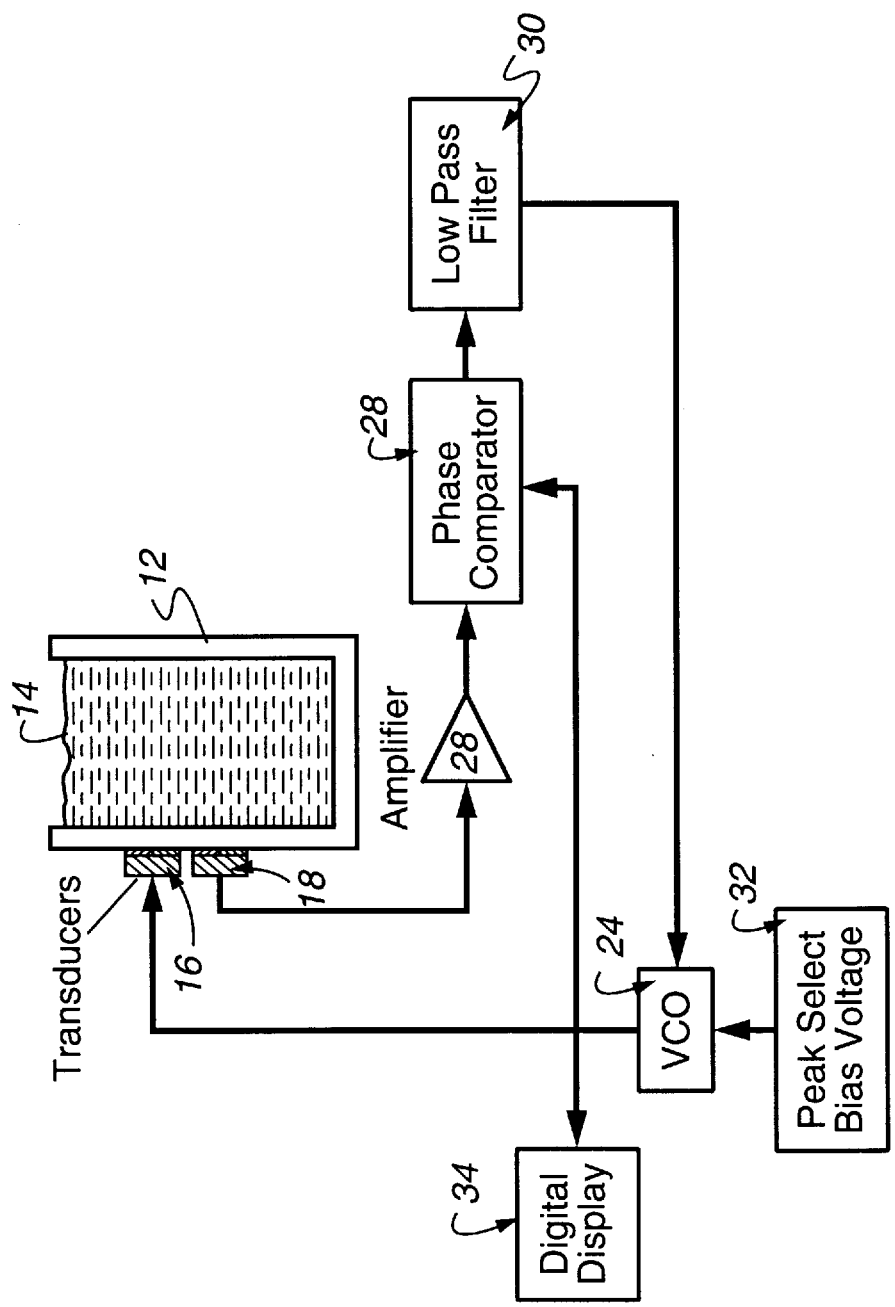
FIG. 4 is a schematic representation of a second embodiment of the apparatus of the present invention suitable for tracking the frequency shift of a sample if the speed of sound therein varies.

Since the variation of gasoline octane manifests itself as a frequency shift in the interference peaks, one may obtain this information by automatically tracking the peak frequency of any particular order interference peak using feedback circuitry. The feedback circuit can be built using integrated circuit chips. A block diagram of a typical circuit useful for this purpose is presented in FIG. 4 hereof This is a feedback circuit. Voltage controlled oscillator 24 drives transducer 16 in the dual-transducer arrangement illustrated. The signal from receiving transducer 18 is first passed through amplifier 26 and then through phase-comparator 28 where it is compared with the output of oscillator 24. The output of phase comparator 28 is filtered through low-pass filter 30, and the resulting dc voltage is fed back to oscillator 24. Bias voltage supply 32 selects the frequency (particular interference peak) to be locked in. The feedback circuit then automatically maintains the lock and the result is displayed digitally in frequency counter 34 which may be calibrated directly in terms of the octane rating. The apparatus will not resonate when there is no liquid present inside receptacle 12. Once gasoline is introduced, however, the apparatus rapidly locks on to the frequency.

Other alternatives to this simple feedback circuit are possible. For example, one can introduce a phase shifter (usually 90°) between oscillator 24 and the phase-comparator 28. This permits the apparatus to lock on the peak value of the particular interference peak. Since the principal interest lies in the frequency shift of the entire pattern, it is not critical that the lock is precisely at the peak position. Locking on the peak becomes critical, however, if a completely different liquid sample is to be analyzed which produces a large sound attenuation. Such liquids introduce changes in interference peak width in addition to the shift in frequency. However, for testing gasolines only of different octane rating, any error due to peak width variation is insignificant. The circuitry described in FIG. 4 hereof can be battery powered and can be packaged in a container the size of a hand-held calculator.

Figure 5:
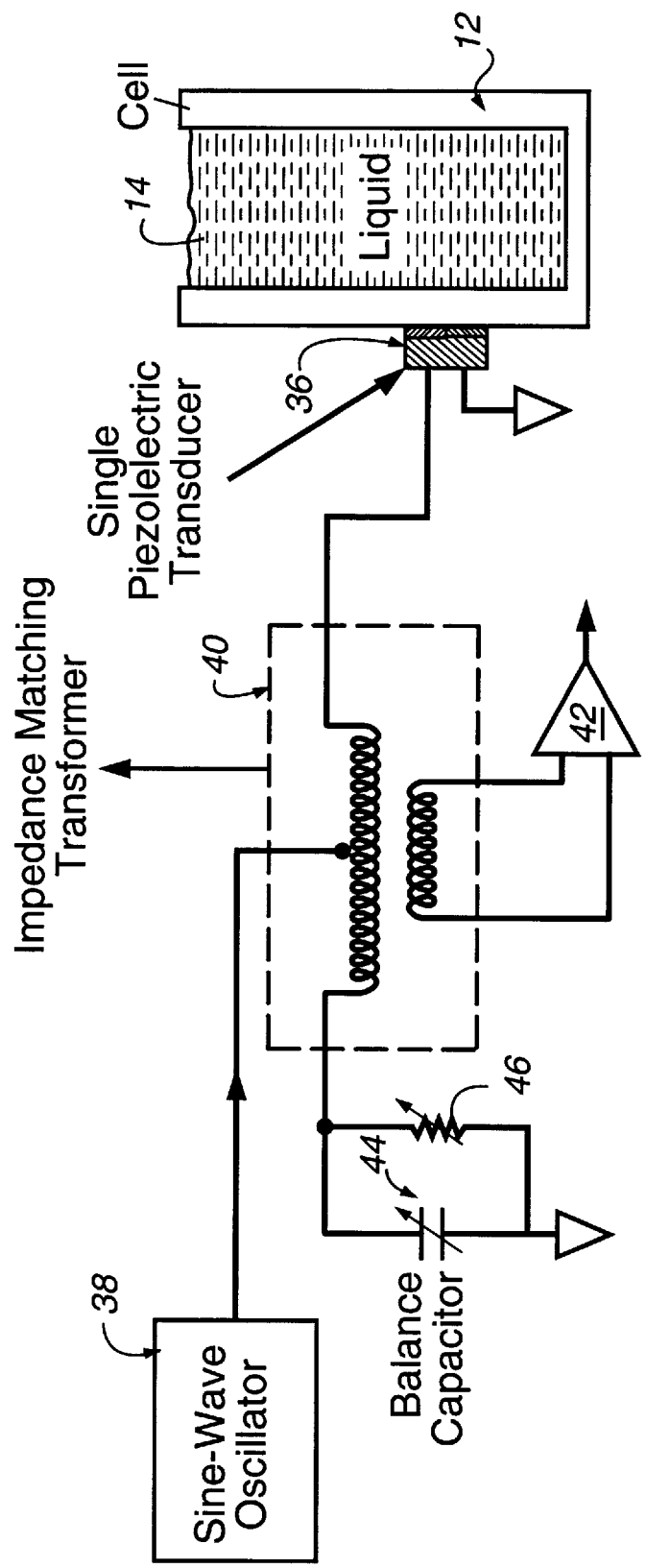
FIG. 5 is schematic representation of a third embodiment of the apparatus of the present invention wherein only a single piezoelectric transducer is used for both impressing an oscillatory signal into the sample to be investigated and for responding to the resonances generated therein.

FIG. 5 is a schematic representation of a third embodiment of the apparatus of the present invention. This embodiment employs but a single transducer 36. Preferably, a piezoelectric disk coated on both sides with electrodes without any damping material associated therewith is used. Transducer 36 is glued to an outside face of receptacle 12. A swept sine wave generated by generator 38 is passed through impedance bridge 40 to transducer 36, and the output therefrom provides a signal which is proportional to the variation of the impedance of the transducer as a function of frequency. As a result of the interference pattern generated in receptacle 12 which provides standing waves at specific frequencies depending upon the speed of sound of the liquid in receptacle 12, the impedance of the transducer is slightly affected. At frequencies corresponding to the interference peaks, less energy is drawn from the crystal, thereby lowering its impedance as seen by the impedance bridge. If the bridge is properly balanced, and amplifier 42 employed, impedance differences may be observed. This balancing process needs to be carried out once by adjusting variable capacitor 44 and variable resistor 46, unless the transducer is changed. It should be mentioned that an automatic frequency tracking system in which a phase-locked loop apparatus locks onto a selected resonance frequency and continuously tracks it can also be employed. Thus, changes in the speed of sound in the liquid would be displayed as a change in frequency on a frequency counter or other appropriate device.

The foregoing description of the invention has been presented for purposes of illustration and description and is not intended to be exhaustive or to limit the invention to the precise form disclosed, and obviously many modifications and variations are possible in light of the above teaching. For example, it would be apparent to one having ordinary skill in the art of transducers, after studying the subject disclosure, that one could also use cylindrical-shaped transducers designed to fit curved surfaces, such as pipes. Another alternative is to use a flat transducer and a shaped matching element designed to couple the flat surface of the transducer to the curved surface of the receptacle, although the sensitivity would be lower than that for a shaped transducer. Additionally, the liquid sample could flow through the receptacle, and the measurements would proceed essentially as described hereinabove, thereby rendering the present invention suitable for monitoring fluids in chemical plants and refineries, as examples. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for comparing corresponding acoustical resonances in liquids, which comprises in combination:
   a. first transducer means for applying a continuous periodic acoustical signal to the outside of a receptacle containing the liquid;
   b. means for sweeping said first transducer means through a chosen frequency range;
   c. second transducer means located on the same side of the receptacle as said first transducer means and in the vicinity thereof, for receiving the acoustical signal generated in the sample; and
   d. means for measuring the resonant frequencies received by said second transducer means.

2. The apparatus as described in claim 1, wherein said first transducer means is driven over a chosen frequency range.

3. Method for comparing corresponding acoustical resonances, said method comprising the steps of:
   a. establishing an acoustic interference pattern in the liquid sample to be investigated by applying a continuous periodic acoustical signal having a chosen frequency to the outside of the receptacle containing the sample;
   b. sweeping the frequency of the applied signal over a chosen frequency range; and
   c. measuring the frequency of the interference peaks in the chosen frequency range.

4. The method as described in claim 3, wherein the acoustical frequency range chosen such that the difference in the interference patterns of liquid samples having different characteristics is maximized.

5. The method as described in claim 3, further including the step of comparing the frequency measured in said step of measuring the frequency with the corresponding frequency for a liquid sample having known acoustical frequency resonance spectrum.

* * * * *